United States Patent [19]

Johnson

[11] 4,046,910

[45] Sept. 6, 1977

[54] DOSAGE SCHEDULE

[75] Inventor: Herbert G. Johnson, Kalamazoo, Mich.

[73] Assignee: The Upjohn Company, Kalamazoo, Mich.

[21] Appl. No.: 677,514

[22] Filed: Apr. 14, 1976

Related U.S. Application Data

[63] Continuation of Ser. No. 436,996, Jan. 28, 1974, abandoned, which is a continuation-in-part of Ser. No. 323,158, Jan. 12, 1973, abandoned, which is a continuation-in-part of Ser. No. 278,275, Aug. 7, 1972, abandoned.

[51] Int. Cl.$^2$ .................. A61K 31/35; A61K 31/385
[52] U.S. Cl. ..................................... 424/278; 424/283
[58] Field of Search ................................ 424/278, 283

[56] References Cited

U.S. PATENT DOCUMENTS 3,419,578  12/1968  Fitzmaurice et al. ............. 260/345.2

OTHER PUBLICATIONS

Howell, "The Practitioner," 208, 750 (1972).
Herzig, 150 Internatl. Cong. Immunology, Washington Workshop 78, Aug. 4, 11971.
Int. Arch. Allergy 41, pp. 161–162 (1971).
Medical Journal of Australia, No. 26., 1382–1386 (1971).
Kusner, Fed. Proc., 31, 533 (1972).
The Medical Journal of Australia, Oct. 9, 1971 pp. 736–757.
Ibid, Nov. 13, 1971, p. 1042.
Schwelz, Med. Wochenschr., 101, No. 25, 934–940 (1971).

*Primary Examiner*—Stanley J. Friedman
*Attorney, Agent, or Firm*—Martin B. Barancik

[57] ABSTRACT

A dosing schedule for Disodiumcromoglycate and Disodiumcromoglycate biologues whereby a substantially smaller dosage is required to bring about effective allergy inhibition. Compositions are also provided.

8 Claims, No Drawings

DOSAGE SCHEDULE

CROSS REFERENCE TO RELATED APPLICATIONS

This is a continuation of application Ser. No. 436,996, filed Jan. 28, 1974, now abandoned which is a continuation-in-part application of our copending application Ser. No. 323,158, filed on Jan. 12, 1973, which is a continuation-in-part of our application Ser. No. 278,275, filed Aug. 7, 1972, both now abandoned.

DESCRIPTION OF THE PRIOR ART

Allergic conditions in mammals have been treated in a number of ways. Desensitization, a technique which attempts to interfere with the antigen-antibody interaction, is commonly employed. Bronchodilators and corticosteroids have been used efficaciously in the anti-asthma area. Recently a new drug, cromolyn sodium, the disodium salt of 1,3-bis(2-carboxychromon-5-yloxy)-2-hydroxypropane, and otherwise known as disodium cromoglycate, is being used for treatment of allergic conditions. This drug, sold in England and other countries under the tradename "INTAL" will hereinafter be referred to as DSCG. DSCG, administered in a prophylactic manner, provides relief from allergic and anaphylactic conditions. For example, prior to entering an area with high air borne pollen concentration, an asthmatic individual may administer a dose of DSCG. This drug has been so effective that many journal reporters have noted patients' dependence on corticosteroids and other anti-allergy medicaments is substantially reduced or eliminated. However, in a significant number of individuals, the administration of the drug appears to be accomplished by a problem. Although the first dose or doses of DSCG seems to bring about a clinically satisfactory inhibition of allergic manifestations, continuing administration of the drug at the same dose level can bring about lower levels of inhibition which may be clinically ineffective. No satisfactory explanation of this phenomenon has been advanced to date.

A dosing schedule has now been discovered which provides a means of obtaining similar or sometimes even higher allergy inhibition levels but with a markedly lower dosage level than employed previously. An obvious advantage of such dosage schedules is that the treated mammal has a lower probability of adverse side reactions since less drug is employed.

BRIEF SUMMARY OF THE DISCLOSURE

In accordance with this invention there is disclosed a method for administering DSCG and DSCG biologues in mammals for the prophylactic treatment of allergy of a reagin or a non-reagin mediated nature which comprises a. administering to a mammal a priming dose of DSCG or DSCG biologue which provides effective inhibition of allergy manifestation, and thereafter b. administering to the mammal treated in step (a), a maintenance dose of DSCG or DSCG biologue, said maintenance dose quantity providing greater inhibition of allergic manifestations in the maintenance dose situation than in the priming dose situation.

A further aspect of this invention is pharmaceutical compositions delivering a therapeutically effective quantity of DSCG or DSCG biologue, said quantity providing greater inhibition of allergic manifestations in the maintenance dose situation than in the priming dose situation.

DETAILED DESCRIPTION OF THE INVENTION

DSCG is a bis cromone species of a genus of compounds disclosed in U.S. Pat. No. 3,419,578. These compounds have the ability to prophylactically protect a mammal from allergic manifestations caused by antigen-antibody interaction. Structurally analogous compounds to DSCG disclosed in U.S. Pat. Nos. 3,519,652, 3,673,218, and 3,484,445 have this ability as well. Compounds structurally nonanalogous to DSCG, such as those compounds disclosed in U.S. Ser. No. 233,772, for example, the tris(hydroxymethyl)aminomethane salts of 10-chloro-1, 4,6,9-tetrahydro-4,6-dioxopyrido[3,2-g]quinoline, 2,8-dicarboxylic acid and 1,4,6,9-tetrahydro-10-methyl-4,6-dioxopyrido[3,2-g]quinoline-2,8-dicarboxylic acid; and U.S. Ser. No. 261,524, for example, the tris(hydroxymethyl)aminomethane salt of 1,1',4,4'-tetrahydro-4,4'-dioxo[6,6'-biquinoline]-2,2'-dicarboxylic acid also have this ability to prophylactically protect against allergic manifestations. The pharmacological mode of action of these drugs appears to be through inhibition of the release of mediators of anaphylaxis. For the purposes of this specification and appended claims, drugs which possess this ability to protect prophylactically against allergic manifestations through inhibiting the release of mediators of anaphylaxis will be referred to hereinafter as "biologues of DSCG."

A DSCG bilogue is characterized and determined by the following biological tests and results thereof.

The compound under review is first tested in the rat passive cutaneous anaphylaxis test system. This test is employed to determine if the compound does inhibit allergic manifestations. A DSCG biologue will inhibit allergic manifestations. The anti-allergy activity of DSCG biologues vary. However, if the compound under study does not show significant inhibition of allergic manifestations at 20 mg./kg. intraperitoneally (i.p.) or intravenously (i.v.) in the rat passive cutaneous test system, its activity is generally too low for practical usage.

Since the rat passive cutaneous anaphylaxis test alone does not indicate what pharmacologic mode of action is being exhibited, various other biological tests are required to show that the compound exhibits its anti-allergy activity as an inhibitor of mediators of anaphylaxis when administered at that dosage rather than in a different pharmacologic manner, that is, as an end organ antagonist, cholinergic or anti-cholinergic and adenyl cyclase stimulator. Thereof, tests to see if the compound inhibits the effect of histamine, serotonin, and slow reacting substance of anaphylaxis (SRSA), that is, that the compound is an end organ antagonist of the mediators, are employed. These are any of the standard well-known biological tests such as contraction of guinea pig ileum in the presence of mepyramine for SRSA activity and contraction of guinea pig ileum in the presence of methylsergide, sometimes known as Desernil, for serotinin activity. If activity is still observed in these systems, it is due to histamine action. A further check on histamine is through the spectrafluorimetric assay described by Shore, Burkhalter and Cohn. Journal of Pharmacology and Experimental Therapeutics, Vol. 127, pg. 182.

Tests for anti-bradykinin activity can also be run, although the results may not be as significant since the role of bradykinin as a mediator of anaphylaxis is equivocal. A DSCG biologue will not be an end organ antagonist.

If the results from these tests show the compound is not an end organ antagonist of the mediators, that is, an antihistamine, then further tests should be run to show that the compound is not exhibiting its activity through cholinergicity or anti-cholinergicity as by the reversal of acetylcholine induced guinea pig tracheal chain contraction. A DSCG biologue will not be a cholinergic or anti-cholinergic. Neither should the compound be an adenyl cyclase activity stimulator, although this may be somewhat equivocal, since the role of cyclic adenosine monophosphate levels in asthma has not been firmly established at this time.

Compounds which provide appropriate results in the above tests are DSCG biologues and included within the priming-maintenance dose schedule disclosed in this application. Examples of compounds which are DSCG biologues have been disclosed earlier in this application. Examples of compounds which are not DSCG biologues but which respond appropriately to some of the tests but not all of them are various prostaglandins, such as Prostaglandin $E_1$ and Prostaglandin $E_2$.

Another element which is significant is assessing whether or not the given compound is a DSCG biologue in its serum life. Compounds which exhibit this activity usually have short serum lives. DSCG serum half life in man is approximately 2 minutes.

The above biological tests may not have an accuracy of 100% in characterizing compounds which have their effecacy spared by the priming-maintenance dose schedule disclosed in this application. If there is doubt about a particular compound, the dosing schedule of the invention can be attempted in the rat passive cutaneous anaphylaxis of system. If the results are positive, the compound is a DSCG biologue for the purposes of this invention.

As stated previously, the amount of DSCG or DSCG biologue required to maintain a mammal in an effective state of allergy prophylaxis can be reduced markedly when the dosage schedule of this invention is followed. After the mammal has received a priming dose of DSCG or DSCG biologue, effective allergy inhibition is achieved with a maintenance dose of DSCG of DSCG biologue which is frequently 1/200 or even lower than that of the heretofore practiced dosage.

It is important to note that the compound used for the priming dose and the compound used for the maintenance does need not be the same. The sparing effect is seen if the priming compound is DSCG and the maintenance compound a DSCG biologue, the priming compound is a DSCG biologue and the maintenance compound is DSCG, the priming compound is one DSCG biologue and the maintenance compound is a different DSCG biologue, or the priming and maintenance compound is the same DSCG biologue.

This highly unusual therapeutic response is apparently due to the fact that a priming dose of DSCG or DSCG biologue is administered initially. For some unknown reason, the initial priming dose or doses appear to spare the quantity of the later maintenance dose(s). The initial priming dose or doses should be of such a quantity that an effective level of inhibiting of allergic manifestation is obtained. The dosage of DSCG presently employed in the treatment of asthma is 20 mg., administered by insufflation every 4 to 6 hours. An additional advantage of obtaining as high a level of inhibition as possible, other than the relief of allergic manifestations of the treated mammal, is that in some cases the higher the allergy inhibition level of the priming dose, the more efficacious a given quantity of DSCG or DSCG biologue is in the maintenance dose situation. It is, of course, preferred to use as little priming dose as possible to obtain an equivalent effect, that is, for example, when the dosage is at the 100 percent allergy inhibition level, the smallest quantity which provides the 100 percent inhibition can be employed.

After the thermal is primed with DSCG or DSCG biologue, a maintenance dose of DSCG or DSCG biologue is administered.

This maintenance dose can be administered in a similar time sequence as the priming dose. For example, asthma under present DSCG dosing schedules is treated every 4 to 6 hours with 20 mg. of DSCG. The quantity of active compound employed in the maintenance dose is directly related to the sparing effect. A quantity which provides a therapeutic response for allergy inhibition up through a quantity which provides more allergy inhibition when given in the maintenance dose situation than in the priming does situation, that is, its drug dosage is spared, can be employed. The point where this break in dosage occurs can be readily observed, as shown from the type of data disclosed further in this application. Generally, a maintenance dose of from about 0.1 to about 20 percent of the priming dose, more specifically from about 1 to about 10 percent, on a molar basis, can be employed when the priming and maintenance compound are the same. When priming and maintenance compounds differ, the maintenance dose is calculated as if the priming compound where the same as the maintenance compound. The actual maintenance dose to be administered is decided upon by the attending medical officer since individual mammals may differ in response. As substantial a therapeutic response as possible for the continuing maintenance doses is, of course, desired.

When the allergy inhibition effect of the maintenance dose declines substantially in the judgement of the medical officer, or the sparing effect is no longer observed, the mammal can be given the usual priming dose once more to initiate another priming-maintenance dose schedule treatment period.

The priming maintenance dose schedule of this invention has the further advantage of substantially reducing the number of mammals who become less responsive to continual DSCG administration at the heretofore employed dosage. If mammals are in this less responsive state due to heretofore practiced DSCG dosing, maintenance doses of DSCG or DSCG biologue can be effective in inhibiting allergic manifestations. If the inhibition levels of the maintenance dose declines substantially or is no longer effective the priming-maintenance dose schedule of this invention can be reinitiated.

The following examples are intended to exemplify the invention and are in no manner intended to limit the invention.

EXAMPLE 1

The following procedures are employed in the subsequent rat PCA tests unless otherwise stated:

Female Sprague-Dawley 250 gm. rats are skin-sensitized with rat anti-ovalbumin homocytotropic antibody that is heat labile and has a passive cutaneous anaphylaxis titer of (1:128). After a 72-hour latency period, the animals are challenged i.v. with a 4 mg. ovalbumin (OA) + 5 mg. Evans blue dye. Thirty minutes later the extravascular bluing that results from antigen antibody combination at the skin site is read. Antibody dilutions are used such that in control animals a 4 mm spot in the lowest detectable spot, and 4 or 5 lower dilutions are used to give a range of antibody in each animal. Four to five animals are used for each variable in the experiment. Percent inhibition of the PCA assay is calculated by comparing the spot scores of DSCG treated rats with the spot scores of control rats. The spot score is the total number of detectable spots over the number of animals.

DSCG Priming Treatment: Passively sensitized rats are injected i.v. 2.0 hours before antigen challenge i.v. Two hours after an i.v. priming dose of 10 mg./kg. DSCG, the rats are challenged with antigen alone. No inhibitory effects are observed.

EXAMPLE 2

The time course of the effective life of DSCG in rats is shown in Table I. DSCG was administered i.p. and was followed by i.v. challenge with 4 mg. ovalbumin and 5 mg. of Evans Blue. Spot score was calculated 30 minutes later from a total of four animals for each time point.

TABLE I

| DSCG 10 mg./kg. | Time of Separation of i.p. Injection & i.v. Challenge | Spot Score | % Inhibition |
|---|---|---|---|
| 0 | — | 2.25 | — |
| + | i.v. at challenge | 0 | 100 |
| + | 5 min | 1.67 | 26 |
| + | 7 | 1.67 | 26 |
| + | 10 | 0.66 | 73 |
| + | 15 | 1.00 | 51 |
| + | 18 | 1.25 | 44 |
| + | 20 | 1.50 | 33 |
| + | 25 | 1.67 | 26 |
| + | 30 | 2.0 | 11 |
| + | 60 | 2.0 | 11 |

These data show that the effect of DSCG does not presist in the animal for extended periods of time. In 30 minutes most of the inhibiting effect of DSCG has disappeared.

EXAMPLE 3

The following table shows the drug sparing effect of previous DSCG treatment on subsequent doses in the rat PCA assay. The animals are rested 2 hours between primary i.v. DSCG injection and i.v. antigen challenge, including secondary DSCG dosing. In view of Table I, this time period is of such a length that the effect from the initial dose of DSCG is not a significant factor. 10 mg./kg. of DSCG given as a priming dose provides an inhibition of 79%. 0.1 mg. of DSCG given as a priming dose does not provide any inhibition.

TABLE II

| | Inhibition in Rat PCA | | | |
|---|---|---|---|---|
| Priming DSCG Treatment, No Antigen, Concentration mg./kg. | Secondary DSCG Treatment with 4 mg. OA and 5 mg. Evans Blue. Concentration mg./kg. | | | |
| | 10 | 1.0 | 0.1 | 0 |
| 10 | 51[a] | 51 | 39 | — |
| 1.0 | 98 | 39 | 27 | — |
| 0.1 | 79 | 39 | 2 | — |

[a]This inhibition is the mean percent from 15 animals

The data in Table II demonstrate that far less of a quantity of DSCG is needed to show significant inhibition when this quantity is administered after a DSCG priming dose. In fact, 0.1 mg. of DSCG does not provide any inhibition in the priming situation but provides 39% inhibition in a maintenance dose situation. Furthermore, it is apparent that high doses of DSCG in the priming situation inhibit the action of high doses of DSCG in the secondary dose situation.

EXAMPLE 4

The effect of a time lag between priming doses and secondary doses with regard to the drug sparing effect and the responsiveness of the treated mammal to further treatment with DSCG or a DSCG biologue is shown in Table III. Rats were injected once daily with 10 mg./kg. DSCG for three days. Control rats were also injected with 1.0 ml. of saline at the same time. Twenty and 48 hours after the last dose of DSCG in the three dose series all rats were injected with DSCG. 4 mg. ovalbumin, and 5 mg. of Evans Blue dye.

TABLE III

| | % Inhibition in the Rat PCA | | |
|---|---|---|---|
| Secondary DSCG Dose | Injected i.v. 3 times with 1.0 ml. Saline | 20 hours after last 10 mg. DSCG | 48 hours after last 10 mg. DSCG |
| 10 | 82 | 20 | 73 |
| 5.0 | 47 | 20 | 65 |
| 1.0 | 11 | 58 | C |
| 0.1 | 0 | 52 | 0 |
| 0.05 | — | 47 | 2 |
| 0 | — | — | 0 |

The data in Table III demonstrate that the drug sparing effect from the priming dosage is present at 20 hours post priming but has disappeared at 48 hours post priming wherein the full effect of the DSCG is noted. It is interesting to note that the predosing schedule, i.e., priming, used in this table brings about greater inhibition of secondary doses than shown in Table III. Moreover, the drug sparing effect of secondary dosage shown in Table III is so great that the therapeutic effect of the secondary doses is greater than the inhibited secondary doses of Table II.

EXAMPLE 5

Th sparing effect using a DSCG biologue, the tris(hydroxymethyl)aminomethane salt of 10-chloro-1,4,6,9-tetrahydro-4,6-dioxopyrido[3,2-g]quinoline-2,8-dicarboxylic acid, referred to as Compound 10 Cl in this Example, is shown in the rat PCA of Table IV. When using this compound in a priming situation, 2.0 mg./kg., 1.0 1 mg./kg., 0.025 mg./kg. and 0.01 mg./kg. give inhibitions of 93, 86, 44 and 0% respectively. The data of Table IV are obtained in the usual manner except that a 48 hour instead of a 72 hour sensitization period was used.

TABLE IV

| | % Inhibition in Rat PCA | | | |
|---|---|---|---|---|
| Priming Dose Compound 10 Cl mg./kg. | Secondary Dose Compound 10 Cl mg./kg. | | | |
| | 2.0 | 1.0 | 0.025 | 0.01 |
| 2.0 | 6 | 14 | 33 | 52 |
| 1.0 | 52 | 44 | 44 | 44 |
| 0.025 | 62 | 52 | 23 | 6 |
| 0.01 | 80 | 71 | 44 | 6 |

The data of Table IV show that sparing is seen with the DSCG biologue Compound 10 Cl at 0.01 mg./kg. maintenance dose level when primed with either 2.0 or 1.0 mg./kg. of Compound 10 Cl.

The data of the above tables demonstrate that compositions of DSCG or DSCG biologue which were heretofore thought to contain insufficient quantities of active compound to provide significant therapeutic responses can provide effective allergy inhibition if given in accordance with the dosing schedule of this invention. The effect of the dosing schedule is most dramatically observed where the quantity of active compound is insufficient to provide any allergy inhibition in the priming situation but provides significant allergy inhibition when used in the maintenance situation.

When the procedures of the above examples are carried out with various combinations of DSCG and DSCG biologues, similar drum spring effects in the maintenance dose situation are obtained. Various drug combinations such as priming with DSCG and maintaining with the tris(hydroxymethyl)aminomethane salt of 10-chloro-1,4,6,9-tetrahydro-4,6-dioxopyrido[3,2-g]quinoline-2,8-dicarboxylic acid; priming with the tris(hydroxymethyl)aminomethane salt of 10-chloro-1,4,6,9-tetrahydro-4,6-dioxopyrido[3,2-g]quinoline-2,8-dicarboxylic acid and maintaining with DSCG; priming and maintaining with the tris(hydroxymethyl)aminomethane salt of 1,1',4,4'-tetrahydro-4,4'-dioxo[6,6'-biquinoline]-2,2'-dicarboxylic acid; priming with tris(hydroxymethyl)aminomethane salt of 1,4,6,9-tetrahydro-10-methyl-4,6-dioxopyrido[3,2-g]quinoline, 2-8-carboxylic acid and maintaining with the sodium salt of 1,1',4,4'-tetrahydro-4,4'-dioxo[6,6'-biquinoline]-2,2'-dicarboxylic acid are illustrative of drug combinations within this invention.

The compositions in which DSCG or DSCG biologue can be employed in this invention are the usual compositions employed in the treatment of allergy and anaphylactic reaction with these compounds. The DSCG compositions are disclosed in U.S. Pat. No. 3,419,578. Compositions of DSCG structurally analogous compounds are disclosed in the previously cited patents. Compositions of nonstructurally analogous compounds are also disclosed in previously cited patent applications.

As state previously, the administration of the priming and maintenance doses of this invention timewise, that is, length of time between doses, is the same as with previous treatments of DSCG or DSCG biologue.

Following are additional examples showing the time dosing schedule and other parameters.

EXAMPLE 6

PRIMING DOSE

A lot of 10,000 tablets, each containing 20 mg. of DSCG is prepared from the following types and amounts of ingredients:

| DSCG | 200 Gm. |
|---|---|
| Dicalcium phosphate | 1,300 Gm. |
| Methylcullulose, U.S.P. (15 cps.) | 60 Gm. |
| Talc | 150 Gm. |
| Corn Starch | 200 Gm. |
| Magnesium stearate | 12 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

MAINTENANCE DOSE

A lot of 10,000 tablets, each containing 0.2 mg. of DSCG is prepared from the following types and amounts of ingredients:

| DSCG | 2 Gm. |
|---|---|
| Dicalcium phosphate | 1,500 Gm. |
| Methylcellulose, U.S.P. (15 cps.) | 60 Gm. |
| Talc | 150 Gm. |
| Corn Starch | 200 Gm. |
| Magnesium stearate | 12 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing food allergy attacks in humans at a dose of 1 priming dose tablet followed by one maintenance dose tablet every 4 hours.

EXAMPLE 7

PRIMING DOSE

One thousand two-piece hard gelatin capsules, each containing 1 mg. of the tris(hydroxymethyl)aminomethane salt of 10-chloro-1,4,6,9-tetrahydro-4,6-dioxopyrido[3,2-g]quinoline-2,8-dicarboxylic acid are prepared from the following types and amounts of ingredients:

| Tris(hydroxymethyl)aminomethane salt of 10-chloro-1,4,6,9-tetrahydro-4,6-dioxopyrido[3,2-g]quinoline-2,8-dicarboxylic acid | 1 Gm. |
|---|---|
| Talc | 180 Gm. |
| Magnesium Stearate | 10 Gm. |

The ingredients are mixed well and filled into capsules of the proper size.

MAINTENANCE DOSE

One thousand two-piece hard gelatin capsules, each containing 0.01 mg. of the tris(hydroxymethyl)aminomethane salt of 10-chloro-1,4,6,9-tetrahydro-4,6-dioxopyrido[3,2-g]quinoline-2,8-dicarboxylic acid prepared from the following types and amounts of ingredients:

| Tris(hydroxymethyl)aminomethane salt of 10-chloro-1,4,6,9-tetrahydro-4,6-dioxopyrido[3,2-g]quinoline-2,8-dicarboxylic acid | 0.01 Gm. |
|---|---|
| Talc | 200 Gm. |
| Magnesium stearate | 10 Gm. |

The ingredients are mixed well and filled into capsules of the proper size.

Capsules so prepared are useful for food allergy attacks in humans at a dose of one priming dose capsule followed by one maintenance dose capsule every 4 to 6 hours.

EXAMPLE 8

PRIMING DOSE

A sterile preparation suitable for intramuscular injection and containing 10 mg. of the tris(hydroxymethyl)aminomethane salt of 1,1', 4,4'-tetrahydro-4,4'-dioxo[6,6'-biquinoline]-2,2'-dicarboxylic acid in each milliliter is prepared from the following ingredients:

| | |
|---|---|
| Tris(hydroxymethyl)aminomethane salt of 1,1',4,4'-tetrahydro-4,4'-dioxo-[6,6'-biquinoline]-2,2'-dicarboxylic acid | 10 Gm. |
| Benzyl benzoate | 200 ml. |
| Methylparaben | 1.5 Gm. |
| Propylparaben | 0.5 Gm. |
| Cottonseed oil q.s. | 1,000 ml. |

MAINTENANCE DOSE

A sterile preparation suitable for intramuscular injection and containing 0.2 mg. of the tris(hydroxymethyl)aminomethane salt of 1,1',4,4'-tetrahydro-4,4'-dioxo[6,6'-biquinoline]-2,2'-dicarboxylic acid in each milliliter is prepared from the following ingredients:

| | |
|---|---|
| Tris(hydroxymethyl)aminomethane salt of 1,1',4,4'-tetrahydro-4,4'-dioxo-[6,6'-biquinoline]-2,2'-dicarboxylic acid | 0.2 Gm. |
| Benzyl Benzoate | 200 |
| Methylparaben | 1.5 Gm. |
| Propylparaben | 0.5 Gm. |
| Cottonseed oil q.s. | 1.000 ml. |

One milliliter of the priming dose is given followed by 1 ml. of maintenance dose every 4 to 12 hours for prophylactic treatment of allergic rhinitis in humans.

EXAMPLE 9

PRIMING DOSE

A powder mixture consisting of 2 grams of DSCG and sufficient lactose to make 5 grams of mixture is micropulverized and 50 mg. of powder placed in a capsule designed for placement in an insufflator to deliver 50 mg. of powder per dose.

MAINTENANCE DOSE

A powder mixture consisting of 40 milligrams of DSCG and sufficient lactose to make 5 grams of mixture is micropulverized and 50 mg. of powder placed in a capsule designed for placement in an insufflator to delier 50 mg. of powder per dose.

A priming dose capsule is administered first and then a maintenance dose capsule every 4 to 6 hours for prevention of asthmatic attacks in humans.

EXAMPLE 10

PRIMING DOSE

A powder mixture consisting of 0.1 gram of the tris(-hydroxymethyl)aminomethane salt of 10-chloro-1,4,6,9-tetrahydro-4,6-dioxopyrido[3,2-g]quinoline-2,8-dicarboxylic acid and sufficient lactose to make 5 grams of mixture is micropulverized and 50 mg. of powder placed in a capsule designed for placement in an insufflator to deliver 50 mg. of powder per dose.

MAINTENANCE DOSE

A powder mixture consisting of 0.005 grams of tris(-hydroxymethyl)aminomethane salt of 10-chloro-1,4,6,9-tetrahydro-4,6-dioxopyrido[3,2-g]quinoline-2,8-dicarboxylic acid and sufficient lactose to make 5 grams of mixture is micropulverized and 50 mg. of powder placed in a capsule designed for placement in an insufflator to deliver 50 mg. of powder per dose.

A priming dose capsule is administered first and then a maintenance dose capsule every 4 to 6 hours for prevention of asthmatic attacks in humans.

EXAMPLE 11

PRIMING DOSE

A power mixture consisting of 2 grams of DSCG and sufficient lactose to make 5 grams of mixture is micropulverized and 50 mg. of powder placed in a capsule designed for placement in an insufflator to deliver 50 mg. of powder per dose.

MAINTENANCE DOSE

A power mixture consisting of 0.005 grams of tris(hydroxymethyl)aminomethane salt of 10-chloro-1,4,6,-9-tetrahydro-4,6-dioxopyrido[3,2-g]quinoline-2,8-dicarboxylic acid and sufficient lactose to make 5 grams of mixture is micropulverized and 50 mg. of power placed in a capsule designed for placement in an insufflator to deliver 50 mg. of powder per dose.

A priming dose capsule is administered first and then a maintenance dose capsule every 4 to 6 hours for prevention of asthmatic attacks in humans.

EXAMPLE 12

Example 9 1 is repeated in its entirety with the exception that the maintenance dose of Example 9 is less than 2 mg. of DSCG. For example, 190 mg. of DSCG is mixed with sufficient lactose to make 5 grams of mixture. The mixture is micropulverized and the powder divided into capsules weighing 50 mg. so as to deliver 1.9 mg. of DSCG per maintenance dose.

EXAMPLE 13

Example 9 is repeated in its entirety with the exception that the maintenance dose of Example 9 is less than 1 mg. of DSCG. For example, 90 mg. of DSCG is mixed with sufficient lactose to make 5 grams of mixture. The mixture is micropulverized and the powder divided into capsules weighing 50 mg. so as to deliver 0.9 mg. of DSCG per maintenance dose.

EXAMPLE 14

Maintenance dose compositions of DSCG to be inhaled, preferably insufflated, are prepared having from about 0.1 to less than 1 mg. of DSCG, preferably from about 0.2 to about 0.9 mg. of DSCG.

EXAMPLE 15

Example 9 is repeated in its entirety with the exception that the maintenance dose of DSCG is 0.02 mg. This is obtained by mixing 2 mg. DSCG with sufficient lactose to make 5 grams of mixture. The mixture is microplverized and the powder divided into capsules weighing 50 mg. so as to deliver 0.02 mg of DSCG per maintenance dose.

EXAMPLE 16

Example 10 is repeated in its entirety with the exception that the maintenance dose of the tris(hydroxymethyl)aminomethane salt of 10-chloro-1,4,6,9-tetrahydro-4,6-dioxopyrido[3,2g]quinoline-2,8-dicarboxylic acid is 0.002 mg. Preparation of the pharmaceutical formulation is carried out by appropriate means.

I claim:

1. A method for administering DSCG in mammals for the prophylatic treatment of allergy of a reagin or non-reagin mediated nature which comprises
   a. administrating to a mammal in need of said treatment a priming dose of DSCG which provides effective inhibition of allergy manifestation, and thereafter
   b. administering to said mammal treated in step (a) an effective maintenance dose of DSCG, said maintenance dose quantity
      1. providing greater inhibition of allergic manifestations in the maintenance dose situation than the same quantity provides in the priming dose situation and
      2. being about 0.1 to about 20% of the quantity of the priming dose.

2. A method in accordance with claim 1 wherein the maintenance dose is continued until the effect of the maintenance dose substantially lessens and thereafter repeating the priming dose-maintenance dose schedule.

3. A method in accordance with claim 1 wherein the priming dose is a quantity necessary to obtain the maximum level of allergy inhibition.

4. A method in accordance with claim 1 wherein the maintenance dose is from about 1 to about 10% of the priming dose.

5. A method in accordance with claim 1 wherein the DSCG is inhaled and the allergy treated is asthma.

6. A method in accordance with claim 4 wherein the DSCG is inhaled and the allergy treated is asthma.

7. A method in accordance with claim 5 wherein the priming dose is 20 mg.

8. A method in accordance with claim 6 wherein the priming dose is 20 mg.

* * * * *